United States Patent [19]
Van Draanen et al.

[11] Patent Number: 5,932,456
[45] Date of Patent: *Aug. 3, 1999

[54] PRODUCTION OF ETHANOL AND OTHER FERMENTATION PRODUCTS FROM BIOMASS

[75] Inventors: Arlen Van Draanen, Bellevue, Wash.; Steven Mello, Bedford, N.H.

[73] Assignee: Ingram-Howell, L.L.C., Haverhill, Mass.

[ * ] Notice: This patent is subject to a terminal disclaimer.

[21] Appl. No.: 08/949,176

[22] Filed: Oct. 10, 1997

Related U.S. Application Data

[63] Continuation-in-part of application No. 08/477,782, Jun. 7, 1995, Pat. No. 5,677,154.

[51] Int. Cl.$^6$ .............................. C12P 7/48; C12P 7/04; C12P 7/06; C12P 7/10
[52] U.S. Cl. .............. 435/144; 435/157; 435/160; 435/161; 435/163; 435/165; 435/171; 435/267
[58] Field of Search ...................... 435/144, 160, 435/161, 163, 165, 157, 171, 267

[56] References Cited

U.S. PATENT DOCUMENTS

| | | |
|---|---|---|
| 2,257,567 | 9/1941 | Matanovich-Manov et al. . |
| 3,557,685 | 1/1971 | Schroering . |
| 3,814,248 | 6/1974 | Lawhead . |
| 3,878,995 | 4/1975 | Nash . |
| 3,888,351 | 6/1975 | Wilson . |
| 3,943,055 | 3/1976 | Korenkov et al. . |
| 4,127,447 | 11/1978 | Griffith et al. . |
| 4,187,775 | 2/1980 | Flender . |
| 4,349,628 | 9/1982 | English et al. . |
| 4,400,470 | 8/1983 | Zeikus et al. . |
| 4,553,977 | 11/1985 | Fry . |
| 4,561,860 | 12/1985 | Gulley et al. . |
| 4,662,569 | 5/1987 | Acker . |
| 4,667,291 | 5/1987 | Weitzman et al. . |
| 4,701,414 | 10/1987 | Van Dijken et al. ................... 435/163 |
| 4,894,066 | 1/1990 | Castelli . |
| 4,985,355 | 1/1991 | Millichip ................... 435/161 |
| 5,000,000 | 3/1991 | Ingram et al. . |
| 5,028,539 | 7/1991 | Ingram et al. . |
| 5,134,944 | 8/1992 | Keller et al. . |
| 5,162,516 | 11/1992 | Ingram et al. . |
| 5,182,199 | 1/1993 | Hartley . |
| 5,250,100 | 10/1993 | Armbristor . |
| 5,407,817 | 4/1995 | Lightsey et al. ................... 435/165 |
| 5,424,202 | 6/1995 | Ingram et al. ................... 435/161 |
| 5,487,989 | 1/1996 | Fowler et al. ................... 435/165 |
| 5,677,154 | 10/1997 | Van Draanen et al. ................ 435/163 |

FOREIGN PATENT DOCUMENTS

| | | |
|---|---|---|
| 0 127 581 | 12/1984 | European Pat. Off. . |
| 6-70782 | 3/1994 | Japan . |
| 1493 480 | 11/1977 | United Kingdom . |
| WO 92/16615 | 10/1992 | WIPO . |

OTHER PUBLICATIONS

"Bioenergy", Bioenergy International, Inc., p. 1–12.
"Ethanol from Biomass: The Five–Carbon Solution", The National Renewable Engergy Laboratory (Feb. 1995).
"Cellulose Conversion Key to Fuel to the Future", The National Renewable Engergy Laboratory (Aug. 1994).
"Joining Forces for Biofuels", The National Renewable Engergy Laboratory (Jan. 1995).

*Primary Examiner*—Herbert J. Lilling
*Attorney, Agent, or Firm*—Choate, Hall & Stewart

[57] ABSTRACT

A method and apparatus for the production of ethanol and other fermentation products including citric acid, butanol and isopropanol from non-virgin biomass having deleterious materials therein is provided. The deleterious materials prevent or retard the production of ethanol and other fermentation products when the non-virgin biomass is combined with a fermentation material. The method includes primary processing, secondary processing and/or blending the non-virgin biomass with virgin biomass such that the effect of the deleterious materials is reduced, thereby allowing production of ethanol and other fermentation products when the biomass is combined with the fermentation material.

5 Claims, 5 Drawing Sheets

PRODUCTION OF ETHANOL AND OTHER FERMENTATION PRODUCTS FROM BIOMASS

PRIORITY CLAIM

The present application is a Continuation-in-part of allowed application U.S. Ser. No. 08/477,782, filed Jun. 7, 1995 now U.S. Pat. No. 5,677,154. The entire contents of this prior application are incorporated herein by reference.

TECHNICAL FIELD

The present invention relates generally to a method and apparatus for the production of fermentation products from biomass, and more particularly to the production of citric acid and other fermentation products such as butanol, isopropanol, ethanol and related chemicals from waste materials.

BACKGROUND OF THE INVENTION

Ethanol has widespread application as an industrial chemical, gasoline additive or straight liquid fuel. As a fuel or fuel additive, ethanol dramatically reduces air emissions while improving engine performance. As a renewable fuel, ethanol reduces national dependance on finite and largely foreign fossil fuel sources while decreasing the net accumulation of carbon dioxide in the atmosphere.

Citric acid has widespread application as a food additive to adjust the pH of foods, as a synergistic antioxidant, and as an industrial chemical in the manufacture of alkyd resins, as a plasticizer and as a sequestering agent to remove trace metals. Isopropanol is also used as an industrial chemical as a solvent, in the composition of antifreeze, as well as in the manufacture of quick-drying inks and oils. Butanol is also used as an industrial chemical as a solvent, including use in industrial cleaning compounds and the like.

Biomass includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables are usually consumed as food. Conversely, biomass high in cellulose, hemicellulose and lignin are not readily digestible and are primarily utilized for wood and paper products, fuel, or are disposed of.

Ethanol and other chemical fermentation products typically have been produced from sugars derived from feedstocks high in starches and sugars, such as corn. While the discussion of fermentation products described herein describes the method and apparatus of the current invention using the example of how the current invention is used to produce ethanol, it will be appreciated by those skilled in the art that the current invention also has application to other fermentation products, including citric acid, butanol and isopropanol and that references to ethanol encompass these other fermentation products.

Recently, the conversion to ethanol of polymeric hexose and pentose sugars in cellulose and hemicellulose has been achieved. See U.S. Pat. No. 4,349,628 to English et al; see also U.S. Pat. No. 4,400,470 to Zeikus et at; U.S. Pat. No. 5,000,000 to Ingram et al; U.S. Pat. No. 5,028,539 to Ingram et al; and U.S. Pat. No. 5,162,516 to Ingram et al, all of which are incorporated herein by reference.

Despite these advancements, certain "non-virgin" forms of biomass have not been successfully utilized in the production of ethanol. For example, municipal solid waste (MSW) as a complex mixture of organic and inorganic materials (approximately 45% paper, 15–20% food and yard waste, 3–5% wood, 12–18% metal and glass, 5–7% plastics and textiles and 5–20% other materials) has certain constituents such as ferrous, non-ferrous and heavy metals, inks, dyes, plastics and clays as well as solvent, pesticide and herbicide residues which can have a deleterious effect on its conversion to ethanol. Similarly, other sources of non-virgin biomass also typically contain deleterious materials which inhibit or prevent their conversion to ethanol.

Disposing of MSW and other non-virgin biomass in an economic and environmentally sound manner is a matter of public concern. Various waste disposal, sorting and recovery systems are known in the art. See e.g., U.S. Pat. No. 2,257,567 to Matanovich-Manov et al; U.S. Pat. No. 3,557,685 to Schroering; U.S. Pat. No. 3,804,248 to Talamantz; U.S. Pat. No. 3,878,995 to Nash; U.S. Pat. No. 3,888,351 to Wilson; U.S. Pat. No. 4,187,775 to Flender; U.S. Pat. No. 4,553,977 to Fry; U.S. Pat. No. 4,561,860 to Gulley et al; U.S. Pat. No. 4,662,569 to Acker; U.S. Pat. No. 4,667,291 to Weitzman et al; U.S. Pat. No. 4,894,066 to Castelli; U.S. Pat. No. 5,134,944 to Keller et al and U.S. Pat. No. 5,250,100 to Armbristor, all of which are incorporated herein by reference. The most common disposal techniques currently utilized by industrial societies are recycling, waste-to-energy conversion and landfilling. Each of these methods has certain disadvantages associated therewith. These disadvantages, including economic and environmental shortcomings, make these techniques less than wholly desirable as a means of disposal.

Recycling can be accomplished through "source separation" wherein wastes are segregated into bins, containers, or "blue bags" by the generator. Alternatively, mixed wastes may be manually and mechanically separated into its constituents without pre-sorting. Recycling programs, although popular, are expensive and inefficient; managing only about 15–25% of municipal solid waste streams. The significant portion of waste materials which cannot be recycled continue to require alternative disposal with attendant infrastructure and cost.

Waste-to-energy conversion is typically accomplished by either preparing from wastes a fuel product for incineration or by "mass-burning" it. These technologies have largely fallen out of favor due to their high cost and negative environmental impact. Moreover, serious air emission and residue toxicity issues remain unresolved giving rise to health and safety concerns.

Landfilling as well, has serious environmental issues associated therewith. For example, landfill gas emissions can be dangerous and toxic leachate can pollute groundwater. Further, landfills often create noxious odors. This technology, although low in cost, results in wasting valuable land, energy and material resources. In many areas where land, energy and material resources are highly valued, there is a trend toward banning the landfilling of wastes.

Various forms of biomass have potential as renewable feedstocks for ethanol production due to their enormous availability and low cost. However, prior attempts to dispose of non-virgin biomass through fermentation to ethanol have been largely unsuccessful. It would therefore be desirable to provide a method and apparatus for the production of ethanol from biomass containing deleterious materials therein, thereby providing an alternative waste disposal technique and overcoming the shortcomings associated with the prior art.

SUMMARY OF THE INVENTION

It is an object of the present invention to provide a method and apparatus for the production of ethanol and other fermentation products from biomass containing deleterious materials therein.

It is another object of the invention to provide a method and apparatus for the production of ethanol and other fermentation products from biomass containing deleterious materials by effectively removing these constituents.

It is another object of the invention to provide a method and apparatus to blend biomass containing deleterious materials with biomass substantially free of these constituents, thereby producing blended biomass in which deleterious materials are effectively diluted such that conversion to ethanol and other fermentation products can be realized.

It is another object of the invention to provide a system for the separation and classification of biomass material for purposes of recycling at least a portion of the material while preparing the remainder for conversion to ethanol and other fermentation products or alternative disposal.

These and other objects of the invention are provided by a method and apparatus in which biomass or non-virgin biomass is converted to ethanol and other fermentation products. The non-virgin biomass initially contains deleterious materials which prevent or inhibit its conversion to ethanol and other fermentation products. The deleterious materials are effectively diminished during separation and processing, thereby allowing for the production of ethanol and other fermentation products. Alternatively, the effect of the deleterious materials in the non-virgin biomass may be effectively diminished with the addition of sufficient virgin biomass such that conversion of the blended biomass to ethanol and other fermentation products can be accomplished. In yet another embodiment of the invention, the non-virgin biomass may be subjected to a secondary processing treatment to further reduce the presence of deleterious materials remaining therein. The non-virgin biomass, which has been subjected to primary and secondary processing, then may be combined with virgin biomass to further reduce the effects of any remaining deleterious materials, or it may be directly converted to ethanol and other fermentation products.

The foregoing has outlined some of the more pertinent objects of the present invention. These objects should be construed to be merely illustrative of some of the more prominent features and applications thereof. Other beneficial results can be attained by applying the disclosed invention in a different manner or modifying it as will be described. Accordingly, other objects and a fuller understanding of the invention may be had by referring to the following Detailed Description of the Invention.

BRIEF DESCRIPTION OF THE DRAWINGS

For a fuller understanding of the present invention, reference is had to the following description taken in conjunction with the accompanying drawings, in which:

FIG. 4(*b*) illustrates a process flow diagram for an alternative method of conversion of biomass and/or blended biomass to ethanol and other fermentation products in accordance with the present invention.

Similar reference characters refer to similar parts throughout the several views of the drawings.

DETAILED DESCRIPTION OF THE INVENTION

Figure 1:
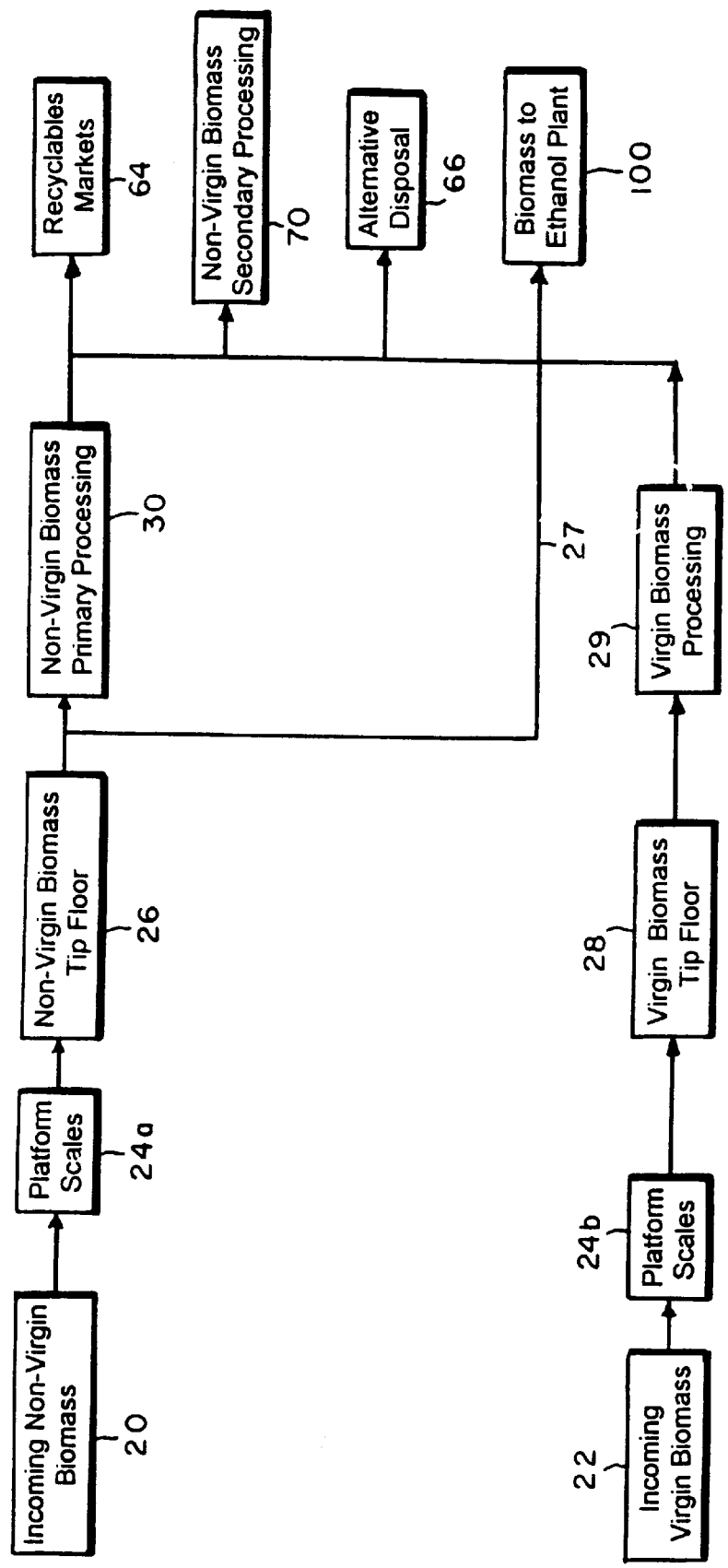
FIG. 1 illustrates a process flow diagram for the preparation of biomass for conversion to ethanol and other fermentation products in accordance with one embodiment of the invention.

While not to be construed as limiting, the terms used herein have the following definitions unless indicated otherwise.

"Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, vines and hard and soft woods (not including woods with deleterious materials). In addition, agricultural biomass includes organic waste materials generated from agricultural processes including farming and forestry activities, specifically including forestry wood waste. Agricultural biomass may be any of the aforestated singularly or in any combination or mixture thereof.

"Biomass" includes virgin biomass and/or non-virgin biomass such as agricultural biomass, commercial organics, construction and demolition debris, municipal solid waste, waste paper and yard waste.

"Blended biomass" is any mixture or blend of virgin and non-virgin biomass, preferably having about 5–95% by weight non-virgin biomass.

"Bulky waste" includes mattresses, sofas, large chairs or other furniture, household appliances or white goods, large industrial scrap, rolls of plastic, motor vehicles including major motor vehicle parts such as automobile transmissions, rear ends, springs and fenders, agricultural and farm machinery and equipment, marine vessels and major parts thereof, and any other large type of machinery, equipment or large type industrial waste.

"Byproducts" are any and all materials other than ethanol or water or ethanol/water mixtures produced or remaining after the conversion of biomass or blended biomass to ethanol.

"Commercial organics" includes beverage industry waste; brewery waste; sweet, acid and salt cheese whey; dairy waste; food processing waste, including potato, chocolate, apple, grape, citrus and other fruit and vegetable pumace; lumber and industrial wood waste; pulp and paper facility waste, including paper sludge; restaurant waste or the like.

"Construction and demolition debris" includes asphalt, brick, concrete, conduit, dirt, flashings, gravel, insulation, masonry, metal, nails, piping, plaster, rock, roofing materials, screws, sheetrock, sheet metal, steel, tar paper, tiles, wire, wood and the like generate from the construction or demolition of commercial or residential structures.

"Conversion" includes any biological, chemical and/or bio-chemical activity which produces ethanol or ethanol and byproducts from biomass and/or blended biomass. Such conversion includes hydrolysis, fermentation and simultaneous saccharification and fermentation (SSF) of such biomass and/or blended biomass. Preferably, conversion includes the use of fermentation materials and hydrolysis materials as defined herein.

"Deleterious materials" includes any organic or inorganic material which has the ability to degrade or limit fermentation materials or hydrolysis materials in any manner, including the prevention or retardation of the hydrolysis conversion of any biomass or its fermentation to ethanol. Examples of deleterious materials include ferrous metals, non-ferrous and heavy metals, grit, dirt, dyes, plastics, clays, solvents, pesticides, herbicides, preservatives, paints, stains, glues, adhesives, and certain phenolic compounds and resins, for example those present in soft wood.

"Ethanol" includes ethyl alcohol or mixtures of ethyl alcohol and water.

"Fermentation products" includes ethanol, citric acid, butanol and isopropanol as well as derivatives thereof.

"Fermentation materials" includes any material or organism capable of producing ethanol. While not to be construed as limiting, the term encompasses bacteria, such as *Zymomonas mobilis* and *Escherichia coli*; yeasts such as *Saccharomyces cerevisiae* or *Pichia stipitis*; and fungi that are natural ethanol-producers. Fermentation materials also encompass engineered organisms that are induced to produce ethanol through the introduction of foreign genetic material (such as pyruvate decarboxylase and/or alcohol dehydrogenase genes from a natural ethanol producer). The term further encompasses mutants and derivatives, such as those produced by known genetic and/or recombinant techniques, of ethanol-producing organisms, which mutants and derivatives have been produced and/or selected on the basis of enhanced and/or altered ethanol production. Preferred fermenting organisms for use in the present invention are ethanol-producing *Zymomonas mobilis* or *Escherichia coli* strains or derivatives thereof. Preferred *Escherichia coli* strains or derivatives thereof are those transformed with recombinant constructs containing a *Zymomonas mobilis* pyruvate dehydrogenase and/or alcohol dehydrogenase gene. Particularly preferred fermenting organisms for use in the present invention are *Zymomonas mobilis* strains from the National Renewable Energy Laboratory that have known ethanol production properties.

"Hazardous waste" includes any material or substance which by reason of its composition or characteristics is toxic or hazardous waste as defined in either the Solid Waste Disposal Act 42 U.S.C. Sections 6901 et seq., as replaced, amended, expanded or supplemented, or any laws of similar purpose or effect, or special nuclear or by-products material within the meaning of the Atomic Energy Act of 1954.

"Hydrolysis materials" includes any material suitable for the hydrolysis of cellulose and hemicellulose to any hexose and pentose sugar, including dilute and concentrated sulfuric acid and enzymes such as those excreted by *Trichoderma reesei*. Particularly preferred hydrolysis materials for use in the present invention are those enzymes from the National Renewable Energy Laboratory that have known hydrolysis properties.

"Municipal solid waste" includes garbage, trash, rubbish, refuse and offal that is normally disposed of by the occupants of residential dwelling units and by business, industrial and commercial establishments, including but not limited to: paper and cardboard, plastics, food scraps, ferrous and non-ferrous metals, wood, lumber, glass, leather, grit or dirt. Municipal solid waste does not include hazardous waste, bulky waste, construction and demolition debris, explosives, pathological and biological waste, radioactive materials, ashes, foundry sand, sewage sludge, cesspool and other human waste or human and animal remains.

"Non-virgin biomass" includes any biomass sample or material, singularly or in combination with another or other materials, which contains one or more deleterious materials in an amount sufficient to degrade or inhibit conversion of the non-virgin biomass to ethanol. Typical examples of non-virgin biomass include but are not limited to most construction and demolition debris, municipal solid waste, hard and soft woods which contain deleterious materials and waste paper.

"Virgin biomass" includes any biomass constituent, singularly or in combination with another or other materials, which is substantially free of deleterious materials. Typical examples of non-virgin biomass include but are not limited to most agricultural biomass (other than certain deleterious soft woods for example), commercial organics and yard waste.

"Waste paper" includes (i) old newspapers (ONP) including unsold and household newspapers; (ii) old corrugated containers (OCC) which include used containers and container plant cuttings; (iii) high-grade de-inking, which includes computer printouts, sorted white office papers, printing plant scrap and printed converting scrap; (iv) mixed paper, which includes paper of varied quality such as unsorted office papers, magazines and unsorted household papers; and (5) pulp substitutes which include various grades of unprinted paper, usually plant scrap.

"Yard waste" includes leaves, twigs, grass, plant cuttings, branches, trees, vines and the like normally disposed of by the occupants of residential dwelling units and by business, industrial and commercial establishments.

It should be appreciated by those skilled in the art that the following separation and process techniques may be controlled utilizing a Digital Control System (hereinafter "DCS"). DCS is capable of controlling the flow rate of various feed materials at various stages of the process. DCS is preferably operated under conditions which allow the various stages of the process to be controlled relative to one another, thereby optimizing continuous operation. While DCS is a preferred mode of controlling the operation of the conversion process in accordance with the present invention, it should also be appreciated that other mechanisms and control devices are suitable for use according to the present invention. For example, flow control valves and the like may be employed where appropriate such that manual control of the operation is possible.

Figure 2:
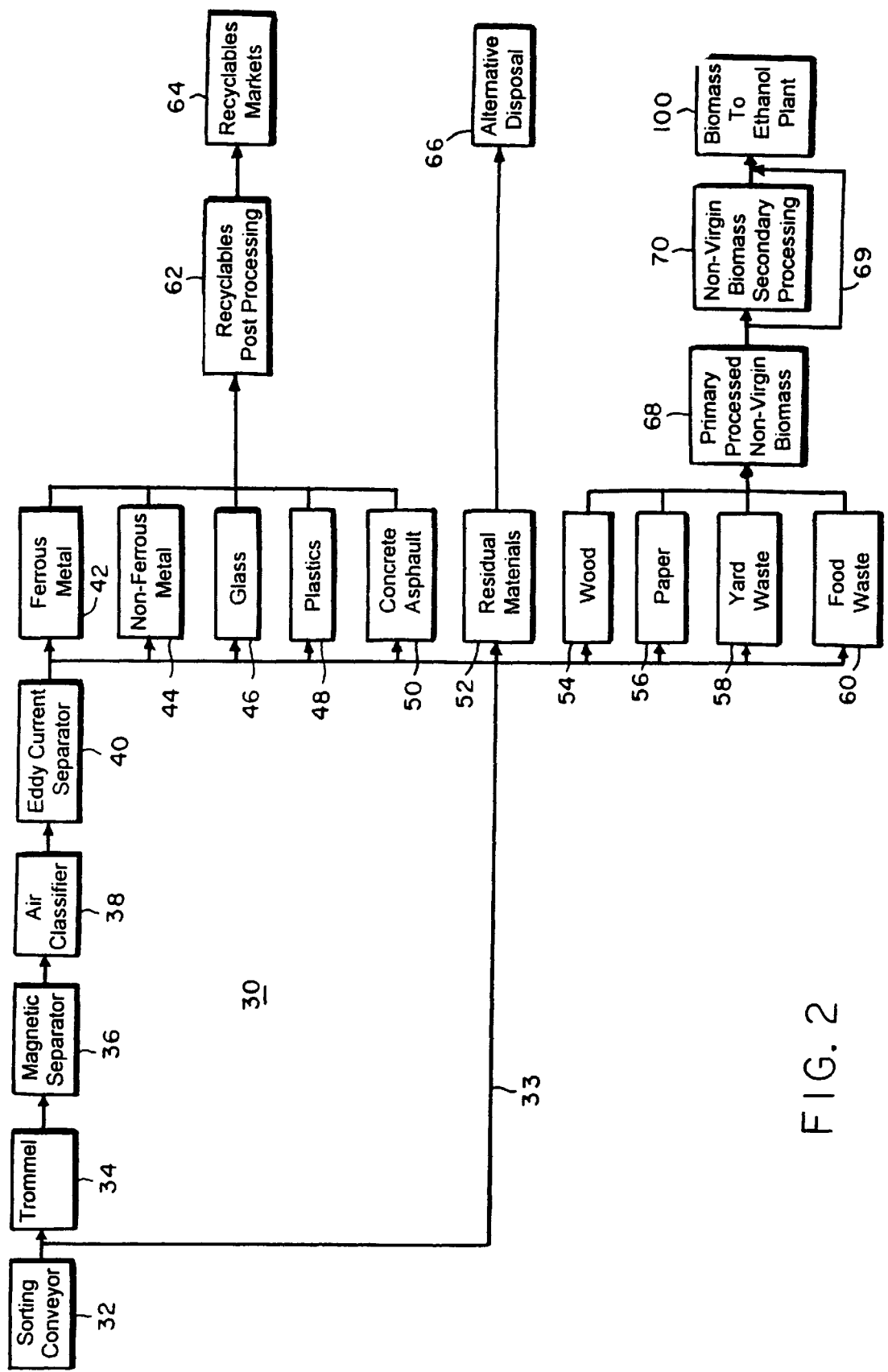
FIG. 2 illustrates a process flow diagram for the primary processing of non-virgin biomass in preparation for conversion to ethanol and other fermentation products.

Referring now to FIG. 1, a process flow diagram for the preparation of biomass for conversion to ethanol in accordance with the invention is shown. Non-virgin biomass 20 enters the biomass separation and preparation facility 10. Non-virgin biomass 20 typically includes municipal solid waste (MSW). Non-virgin biomass 20 alternatively may include construction and demolition debris, waste paper, certain soft woods or combinations thereof including any combination with MSW. Non-virgin biomass 20 is weighed using scales 24a. For example, truck or rail scales such as the type manufactured by Cardinal Scale, Fairbanks Scale or the like are suitable for use in accordance with the present invention. Subsequent to weighing, non-virgin biomass 20 is unloaded from trucks or rail cars onto biomass tip floor 26 and then mechanically pushed by a front end loader or similar device of the type manufactured by Caterpillar Corporation, Volvo-GM or the like. Non-virgin biomass 20 is pushed onto a sorting conveyor or the like manufactured by Heil Engineered Systems and transported to non-virgin biomass primary processing facility 30 as discussed in greater detail herein and as shown in FIG. 2. Alternatively, all or a portion of non-virgin biomass 20 is removed from tip floor 26 and may be forwarded directly to biomass to ethanol plant 100 by a conveyor 27 or the like. Non-virgin biomass 20 which is transported to biomass to ethanol plant 100 via conveyor 27 preferably does not contain large amounts of deleterious materials therein such that conversion to ethanol is more readily attainable than non-virgin biomass 20 containing large amounts of deleterious materials. Preferably, non-virgin biomass 20 containing large amounts of deleterious materials are subjected to non-virgin biomass primary processing 30 and in some instances, secondary processing 70.

As more fully illustrated in FIG. 2, primary processing facility 30 separates non-virgin biomass 20 into various constituents and removes certain deleterious materials therefrom. In particular, primary processing facility 30 illustrated in FIG. 2 facilitates removal of a certain fraction of deleterious materials such as ferrous metals, non-ferrous and heavy metals, inks, dyes, plastics, clays, grit, dirt, solvents, pesticides, herbicides, preservatives, paints, stains, glues and adhesives from non-virgin biomass 20 such that production of ethanol is enhanced or can be attained. A combination of manual separation, trommels, magnets, air classifiers and eddy current separators are utilized as pre-processing devices to separate materials. For example, large deleterious materials such as bulky waste are removed from sorting conveyor 32 early in the process by conveyor 33 or the like. These deleterious materials are later combined with other residual materials 52 containing deleterious constituents and are then transported for alternative disposal 66. Primary processing facility 30 also allows ferrous metals 42, non-ferrous metals 44 such as aluminum, glass 46, plastics 48, concrete and asphalt 50 to be removed from non-virgin biomass 20 and sent to recyclables post processing facility 62. Recyclables post processing facility 62 is equipped to prepare and process these constituents to recyclable markets 64.

Non-virgin biomass primary processing facility 30 also separates non-virgin biomass 20 into residual materials 52 and primary processed non-virgin biomass 68. Primary processed non-virgin biomass 68 typically will include components such as wood 54, paper 56, yard waste 58 and food waste 60. Primary processed non-virgin biomass 68 may be transported for further processing if necessary in non-virgin biomass secondary processing facility 70. Alternately, biomass 68 may be directed to the biomass to ethanol facility 100 by conveyor 69 similar to the type manufactured by Heil Engineered Systems or the like. Residual materials 52, which may include dirt, grit, broken glass and the like, are removed from the process and subjected to alternate disposal 66. Alternate disposal is typically a landfill where this material is suitable for use as landfill cover.

Referring again to FIG. 2, biomass 20 enters facility 30 and is fed via conveyor of the type previously described to trommel 34 of the type manufactured by Heil Engineered Systems. Preferably, bags in the stream are opened by stationary knife-spikes at the trommel drum inlet. The material is sorted as it proceeds through the trommel into three size categories. Each stream is conveyed separately and is subject to magnetic separation to remove ferrous metals and an air classifier and eddy current separator to separate non-ferrous metals, plastics and dirt and grit. Like materials separated in each train are recombined and subject to recyclables processing 62, alternative disposal 66 or are handled as primary processed non-virgin biomass 68 being subject to either secondary processing 70 or transfer to biomass to ethanol plant 100. The train with the largest fraction is also preferably subject to visual inspection and manual separation of larger materials as necessary to enhance the separation process. The manual separation stations preferably are enclosed in a climate-controlled work room and all transfer points throughout the process are vented into a fugitive-dust control system through a fabric filter. Materials subjected to recyclables post processing facility 62 may be cleaned, crushed, shredded and/or baled prior to being forwarded to market 64.

In an alternative embodiment of the invention also illustrated in FIGS. 1, 4(*a*) and 4(*b*), deleterious materials in non-virgin biomass 20 may be diluted by combining virgin biomass 22 with non-virgin biomass 20. Depending on the nature, availability and characteristics of the biomass streams 20 and 22, the present invention provides a process which accepts any relevant input material in combination with any one or more others in order to obtain biomass or blended biomass in which deleterious materials are sufficiently removed and/or diluted to permit conversion of biomass to ethanol.

As shown in FIG. 1, non-virgin biomass 20 is weighed using scales 24*a* and virgin biomass 22 is weighed using scales 24*b*. Scales such as those available from Cardinal Scale, Fairbanks Scale or the like are suitable for use in accordance with the invention. Non-virgin biomass 20 is unloaded on tip floor 26 and virgin biomass 22 is off-loaded to tip floor 28. Non-virgin biomass 20 may be processed and separated as discussed above with reference to FIG. 1 or alternatively may be transported via conveyor 27 or the like directly to biomass to ethanol facility 100. Virgin biomass 22 is transported via a conveyor or the like to virgin biomass processing facility 29 where the material is preferably processed through a shredder of the type manufactured by Heil Engineered Systems, Gruendler Crushers, Eurohansa Inc., or the like. The shredder reduces particle size prior to conveying biomass 22 to biomass to ethanol facility 100 for conversion to ethanol as described in more detail herein and as illustrated in FIGS. 4(*a*) and 4(*b*).

As described above, primary processed non-virgin biomass 68 can be directed to either non-virgin biomass secondary processing facility 70 (shown in greater detail in FIG. 3) or transported directly to biomass to ethanol facility 100 by conveyor 69 or the like for blending as necessary and conversion to ethanol as described in greater detail in FIGS. 4(*a*) and 4(*b*).

Figure 3:
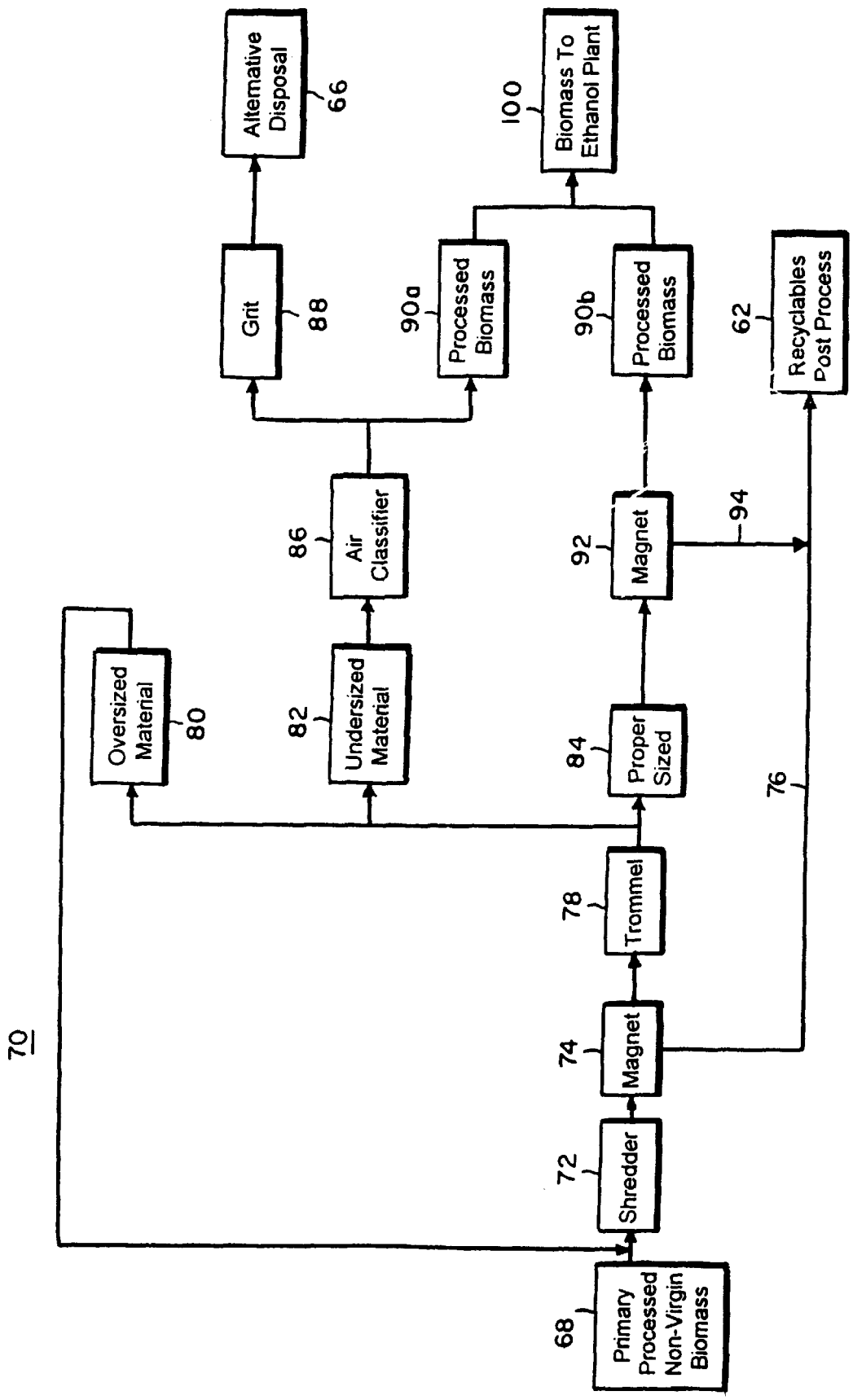
FIG. 3 illustrates a process flow diagram for the secondary processing of non-virgin biomass for conversion to ethanol and other fermentation products in accordance with the present invention.

Referring now to FIG. 3, a method and apparatus for secondary processing of non-virgin biomass to prepare for the conversion to ethanol while removing certain additional deleterious materials to the conversion is shown. Primary processed non-virgin biomass 68 enters facility 70 and is fed to shredder 72. The residue from shredder 72 passes before magnet 74 to remove residual ferrous material. Ferrous material is preferably removed from the process via 76 which may be a conveyor or any other suitable transporting device. The ferrous material preferably is recycled to market 62. It should be appreciated that materials removed during secondary processing 70 typically will be smaller than materials removed during primary processing. The remaining material is then directed to trommel 78 and is separated into three sizes. Trommels manufactured by Heil Engineered Systems or the like, preferably without stationary knives, are suitable for use in the invention. The smallest fraction or undersized material 82 is directed to air classifier 86 where grit 88 is separated from processed biomass 90*a*. Grit 88 is processed and transported to alternative disposal 66 for use as landfill cover. Processed biomass 90a, which contains primarily biomass material with substantially all deleterious materials removed therefrom, may be fed directly to biomass to ethanol plant 100 as shown in FIG. 3. Alternatively, fraction 90a may be combined with fraction 90b and subsequently fed to biomass to ethanol plant 100.

Middle or proper sized fraction 84 is preferably directed before magnet 92 to further remove residual ferrous material, which is removed from the system via 94 which may be a conveyor or any other suitable device. Material 84 is directed as processed biomass 90b to biomass to ethanol plant 100 directly using a conveyor or the like. Processed biomass 90b contains primarily biomass material with substantially all deleterious materials removed therefrom. Alternatively, processed biomass 90b may be combined with processed biomass 90a and fed to biomass to ethanol plant 100 for conversion to ethanol. The largest or oversized material 80 is recycled to shredder 72 for reprocessing until no oversized material remains. Preferably, ferrous material recovered from magnet 74 and/or magnet 92 is directed to the recyclables post processing facility 62.

Figure 4A:
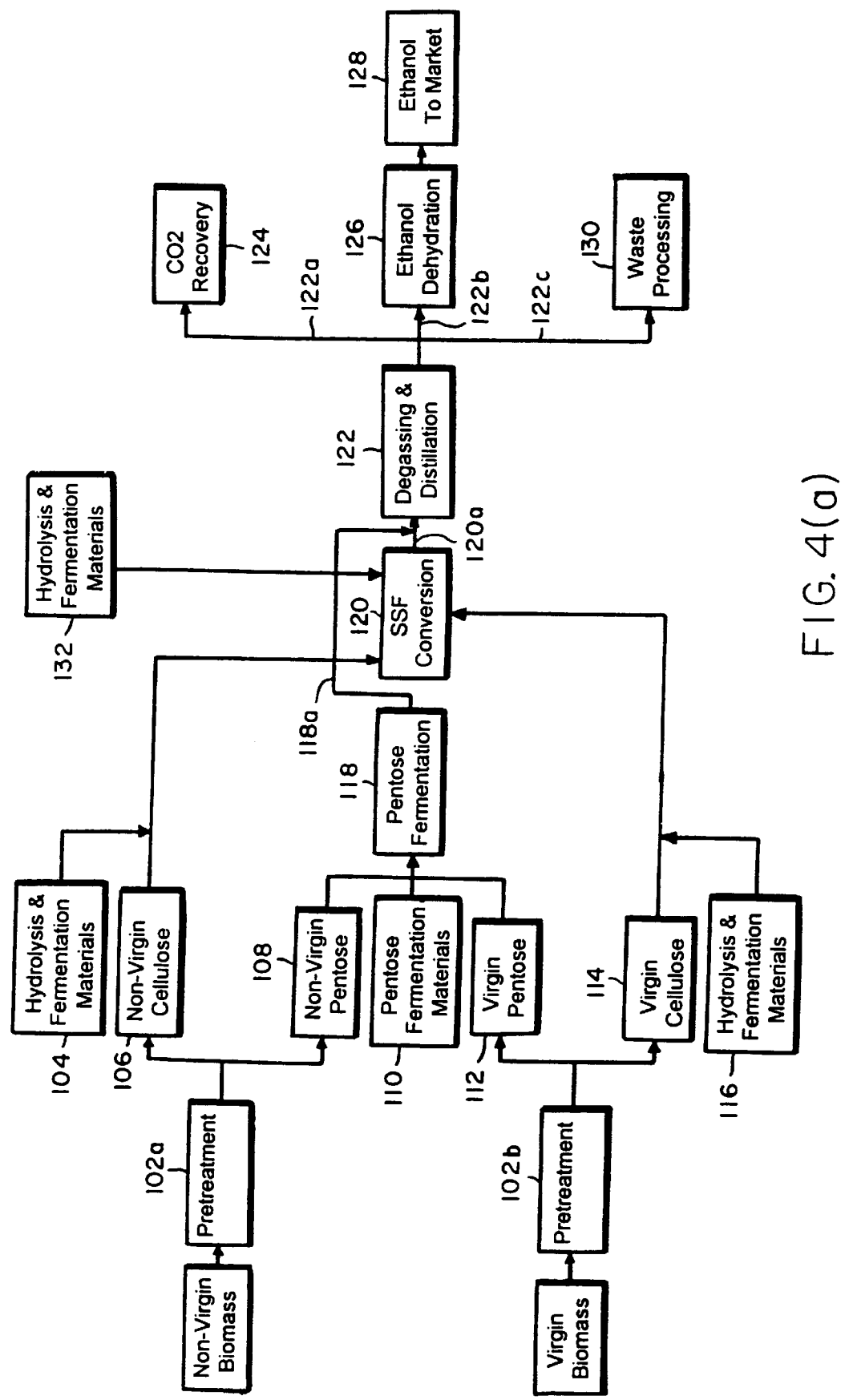
FIG. 4(*a*) illustrates a process flow diagram for the conversion of biomass and/or blended biomass to ethanol and other fermentation products according to the present invention.

A method and apparatus for the conversion of biomass or blended biomass to ethanol is illustrated in FIG. 4(a). Non-virgin biomass enters plant 100 from conveyor 27, conveyor 69 or secondary processing unit 70. Non-virgin biomass is subjected to pretreatment 102a. While not be construed as limiting, pretreatment 102a may include pressure treatment, steam treatment, treatment with dilute and/or concentrated sulfuric acid, screening, liquefaction, pulping, sterilization including the use of oxidizing and/or reducing agents including sodium hypochlorite, ozonolysis, infrared radiation and ultraviolet radiation. Pretreatment can provide for the hydrolysis of hemicellulose to pentose and the expansion of cellulose. Pretreatment may include any combination of the above-mentioned techniques. Pretreatment 102a may be performed in a unit of the type available from Black and Clawson.

Pretreated non-virgin biomass is separated into cellulose 106 and pentose 108. Hydrolysis and/or fermentation materials 104 are added to cellulose 106 such that simultaneous saccharification and fermentation (SSF) in unit 120 occurs. As shown in FIG. 4(a), hydrolysis and fermentation materials 104 may be combined with cellulose 106 prior to entering SSF unit 120. SSF vessels suitable for use in accordance with the present invention include fermentation vessels of the type manufactured by Pfaudler or DeDeitrich. The amount of hydrolysis and fermentation materials 104 added to cellulose 106 are controlled by the Digital Control System (DCS). Suitable DCS are available from Johnson Controls and Bailey Controls. Alternatively, hydrolysis and fermentation materials 132 may be added directly to unit 120 and combined with cellulose 106 therein. Fermentation materials 110 are combined with pentose 108, either prior to or in pentose fermentation unit 118. Vessels suitable for use as fermentation units in accordance with the present invention include fermentation vessels of the type manufactured by Pfaudler or DeDeitrich. The DSC controls the addition and rate of addition of pentose fermentation materials 110 to pentose 108.

If virgin biomass 22 is utilized, virgin biomass 22 preferably enters from virgin biomass processing facility 29 and is subjected to pretreatment 102b. Pretreatment 102b may include any of the pretreatment techniques described above with reference to pretreatment 102a. Virgin biomass may then be separated into pentose 112 and cellulose 114, preferably with a centrifuge of the type manufactured by Sharples or Tolhurst. Pentose 112 is combined with pentose 108 and pentose fermentation materials 110 in such a manner that pentose fermentation occurs in unit 118. Hydrolysis and/or fermentation materials 116 are added to cellulose 114 in such a manner that simultaneous saccharification and fermentation (SSF) in unit 120 occurs. Alternatively, hydrolysis and fermentation materials 132 may be fed directly to SSF conversion unit 120 from unit 132 as shown in FIG. 4(a). As shown in FIG. 4(a), non-virgin cellulose 106 and virgin cellulose 114 are combined in unit 120 and are monitored by the DCS. Preferably, virgin biomass 22 and non-virgin biomass 20 are blended in unit 120. However, the blending of virgin biomass 22 and non-virgin biomass 20 may alternatively be done prior to entering unit 120.

As described above, hydrolysis materials includes any material suitable for the hydrolysis of cellulose and hemicellulose to hexose and pentose sugars, including dilute and concentrated sulfuric acid. In addition, enzymes such as those excreted by *Trichoderma reesei* are suitable for use as hydrolysis materials. As also described above, fermentation materials include any material or organism capable of producing ethanol. Exemplary fermentation materials include, but are not limited to bacteria, yeast and fungi that are natural ethanol-producers. Preferred fermentation materials include *Zymomonas mobilis* and *Escherichia coli*.

Fermented pentose 118a may be combined with SSF product 120a and subjected to distillation and degassing in unit 122. Alternatively, fermented pentose 118 and SSF product 120a may be distilled and degassed separately by utilizing the DCS or by providing flow control valves or the like upstream of the mixing point of stream 118a and 120a and manually controlling such valves.

Distillation and degassing unit 122 allows for the recovery of ethanol and the product exiting distillation and degassing unit 122 is preferably separated into three streams, illustrated in FIG. 4(a) as 122a, 122b and 122c. Suitable distillation and degassing units for use in accordance with the invention include those manufactured by Pfaudler and DeDeitrich. Stream 122a contains primarily carbon dioxide and is transported to $CO_2$ recovery unit 124 or is vented to the atmosphere as appropriate. Stream 122b contains primarily ethanol which may be transported to ethanol dehydration unit 126. The dehydrated ethanol is then transported to market 128. Stream 122c primarily contains waste such as solid byproducts, water, lignin and the like which are separated by centrifuge which are manufactured Sharples and Tolhurst and then dewatered in a press of the type manufactured by Sparkler. These byproducts are preferably transported to waste processing unit 130 for treatment.

Figure 4B:
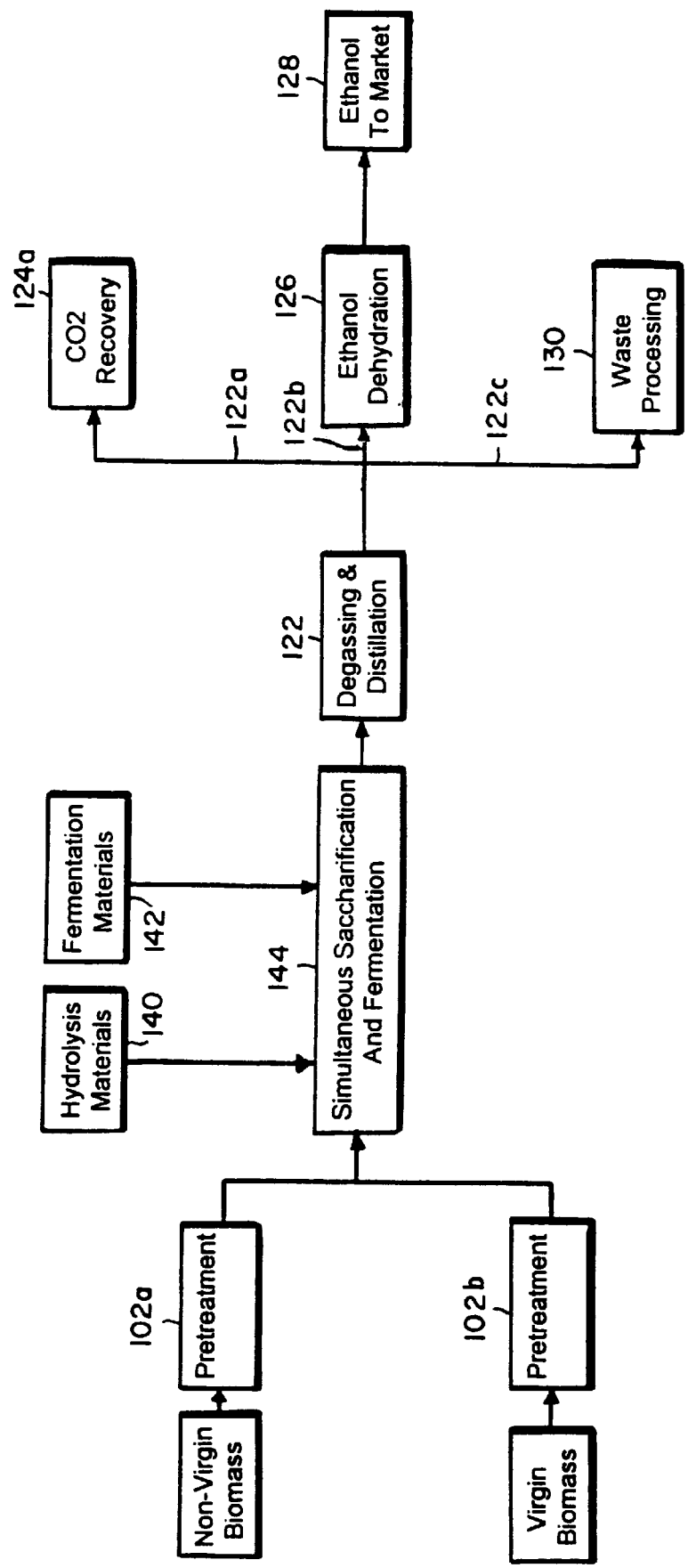

An alternative method and apparatus for the conversion of biomass or blended biomass to ethanol is illustrated in FIG. 4(b). As described above with reference to FIG. 4(a), non-virgin biomass enters plant 100 from conveyor 27, conveyor 69 or secondary processing unit 70. As described above, non-virgin biomass is subjected to pretreatment 102a. If virgin biomass 20 is utilized, biomass 20 preferably enters from virgin biomass processing facility 29 and is subjected to pretreatment 102b. Virgin biomass is then combined with pretreated non-virgin biomass and forwarded to simultaneous saccharification and fermentation (SSF) unit 144 of the type manufactured by Pfaudler and DeDeitrich. Alternatively, virgin biomass and non-virgin biomass may be introduced into SSF unit 144 separately Hydrolysis materials 140 are added to hydrolyze cellulose and fermentation materials 142 are added to unit 144 in an amount sufficient to insure conversion of the biomass and/or blended biomass to ethanol. While not to be construed as limiting, preferable fermenting materials are *Zymomas mobilis* strains and *Escherichia coli* strains. As described above, the addition of materials 140 and 142 are controlled by DCS.

After the conversion process is completed, the product is removed from unit 144 and separated as described above with reference to FIG. 4(*a*).

While not to be construed as limiting, the follow examples illustrate the proposed production of ethanol in accordance with the present invention.

EXAMPLE 1

In this Example, municipal solid waste (MSW) is utilized as non-virgin biomass and is procured from any available source. For example, MSW can be obtained from a compactor truck performing routine pick-up in a rural or urban community or from a transfer station in a like area. The virgin biomass in this Example is a mixture of about 50% hard wood chips, 25% yard waste and 25% paper sludge.

Preparation of Virgin Biomass

The virgin biomass is prepared for conversion to ethanol by feeding the material to a disc refiner where the particle size is reduced to approximately 1–6 millimeters. The material is screened to assure uniformity of size and blended completely. Any material which does not readily screen is re-fed to the disc refiner until the appropriate size is attained. The screened material is fed to a screw conveyor which enters an un-jacketed stainless steel impregnator where dilute sulfuric acid and low pressure steam are injected at ambient pressure. The residence time in the impregnator is expected to be about 5–20 minutes at 80–150° C. When retention is complete, the impregnated material is discharged through a stainless steel rotary valve into a pre-hydrolysis reactor. In the reactor, high pressure steam is directly injected to expose the cellulose for subsequent enzymatic hydrolysis while simultaneously converting the complex hemicellulose to pentose through the action of the impregnated sulfuric acid. In this Example, the material is expected to be held at a pressure of 3.0–8.0 atmospheres at 50–200° C. for between 5–20 minutes prior to being discharged to a stainless steel blowdown tank. Water is added as necessary to cool the material and produce a mixture suitable for pumping. The material is transferred to an agitated stainless steel neutralization tank where excess sulfuric acid is neutralized with 20% aqueous sodium hydroxide. When a pH of approximately 6.0–8.0 is attained, the mixture may be buffered with 0.2 molar potassium phosphate or other suitable buffering agent. The mixture is expected to have a solids of content of approximately 10–20% by weight after neutralization. It is expected that 1.0–4.0% by weight of the neutralized mixture is separated into a sterile stainless hold tank to be utilized for cellulase production necessary for the saccharification of cellulose to hexose. The balance of the material is transferred to an enclosed agitated and jacketed stainless steel vessel for subsequent processing.

Preparation of Non-Virgin Biomass

Non-virgin biomass is prepared for conversion to ethanol by feeding the material to a separate disc refiner where the particle size is reduced to approximately 1–6 millimeters. No other pre-processing or material separation is undertaken in this Example. The material is screened to assure uniformity of size and is blended completely. Any material which does not readily screen is re-fed to the disc refiner until the appropriate size is attained. The screened material is fed to a screw conveyor which enters a separate unjacketed stainless steel impregnation-sterilization vessel where dilute sulfuric acid and low pressure steam are injected at ambient pressure. The residence time in this vessel is anticipated to be between 5–20 minutes at 80–150° C. When retention is complete, the impregnated material is discharged through a stainless steel rotary valve into a separate pre-hydrolysis reactor. In the reactor, high pressure steam is directly injected to expose the cellulose for subsequent enzymatic hydrolysis while simultaneously converting any hemicellulose to pentose through the action of the impregnated sulfuric acid. It is expected that the blend will be held at a pressure of 3.0–8.0 atmospheres at 50–200° C. for 10–25 minutes prior to being discharged to a stainless steel blowdown tank. Water is added as necessary to cool the material and produce a mixture suitable for pumping. The material is transferred to an agitated stainless steel neutralization tank where excess sulfuric acid is neutralized with 20% aqueous sodium hydroxide or other appropriate neutralization agent. When a pH of approximately 6.0–8.0 is attained, the mixture may be buffered with 0.2 molar potassium phosphate or other suitable buffering agent. It is anticipated that the mixture will have a solids content of approximately 10–20% by weight after neutralization. The material is transferred to an enclosed agitated and jacketed stainless steel vessel for subsequent processing.

Separation of Materials

In this Example, separate fermentation of hexose and pentose sugars is employed. Pentose sugars remain in the liquid phase of each mixture previously described while the solid fraction contains largely cellulosic material which require hydrolysis prior to fermentation. The solid and liquid fractions are separated by centrifugation in dedicated systems for the virgin and non-virgin materials. The filtrates are collected in separate stainless steel holding tanks while the cellulosic solid cake is re-slurried in water in separate enclosed agitated stainless steel vessels. The pH of the re-slurried material may be again buffered with potassium phosphate.

Preparation of Cellulase Enzymes

Cellulase enzymes are prepared to be utilized during simultaneous saccharification and fermentation to convert cellulose to hexose sugars. It is expected that about 1.0–4.0% of the mixture prepared from virgin biomass is directed to a stainless steel jacketed and agitated vessel. The temperature of this vessel is preferably maintained below 40° C. with cooling water during fermentation. Seed fermenters feed this vessel with cell mass while air and nutrients are added separately. The cellulase is held in an agitated stainless steel hold tank and is utilized in the next step.

Preparation of Ethanol

The re-slurried cellulosic material is subjected to simultaneous saccharification and fermentation. The pentose sugars in the liquid fraction of the separated materials is subject to fermentation separately.

After assaying the material using known techniques, about forty equivalent parts reslurried cellulosic material from virgin biomass is transferred from the holding tank to a stainless steel jacketed and agitated fermentation vessel. It is expected that an initial charge of one equivalent part re-slurried cellulosic material from non-virgin biomass is made prior to adjusting and holding the temperature within the expected range of 30–45° C. and charging enzymes and bacteria. The pH of the mixture is continuously monitored, adjusted and held within the expected range of 6.0–8.0. Cellulase enzymes produced previously are charged at an expected loading level between 3.0–10.0 international units per gram of cellulose. In this Example, a *Zymomonas*

*mobilis* or *Escherichia coli* strain is employed for fermentation and is charged at this time as well. The hydrolysis and fermentation process is continuously monitored through common gas or liquid chromatographic techniques and the rate of hydrolysis and fermentation is continuously compared to known rates for virgin biomass. After 5–15 hours, it is anticipated that the rate comparison will indicate additional loading of non-virgin material is appropriate. One additional equivalent part is charged and appropriate adjustments to enzyme and bacteria feeds may be made. The fermentation process is expected to continue for a total of 100–200 hours with the rates of conversion being continuously monitored and compared to known virgin material conversion rates. It is expected that the ethanol yield and rate will be approximately the same as those of virgin material conversion within acceptable statistical deviations.

Pentose fermentation is approached similarly, however no cellulase loading is required and either *Zymomonas mobilis* or *Escherichia coli* is utilized for fermentation. In a stainless steel, agitated and jacketed fermentation vessel and the temperature held at within the expected range of 30–45°. The pH of the mixture is continuously monitored, adjusted and held within the expected range of 6.0–8.0. After material assay and initial charges of 40 equivalent parts virgin and 1 equivalent part non-virgin material from their respective holding tanks, bacteria is charged and the fermentation rate is to be followed for 2–10 hours, and one equivalent part non-virgin material is expected to be added. The fermentation process continues for an expected 20–100 hours with rates of conversion being continuously monitored using similar techniques as described above and compared to known virgin material rates. It is expect that the ethanol yield and rate will be approximately the same as those for virgin material conversion within acceptable statistical deviations.

Purification of Ethanol

When fermentation is complete, the effluent streams are directed separately or in combination to an enclosed stainless steel degassing drum where the mixture is heated with agitation to destroy fermenting and hydrolysis materials and release dissolved and entrained carbon dioxide. The carbon dioxide is normally vented to the atmosphere after demisting or it can be recovered using known techniques. After degassing, the effluent is transferred to a separate agitated and jacketed stainless steel vessel equipped with a distillation column whereupon heat is applied and ethanol is recovered with or without vacuum. Alternatively, known beer and rectification column technology may be utilized for ethanol recovery. When distillation is complete, the azeotropic ethanol can be purified using known methods or directly used as a fuel grade material. The still or column bottoms are directed to a centrifuge for separation of solid and liquid materials. Reclaimed solids may be utilized as boiler fuel for process steam needs with the effluent being directed to the wastewater treatment facility.

Waste Treatment

Readily available commercial systems are utilized in treating waste streams generated in this Example. The liquid generated by centrifugation of lignin and other materials after fermentation and distillation is directed to a holding tank and subsequently to an anaerobic digester for conversion of certain organic materials to methane. It is expected that greater than eighty percent of soluble solids, byproducts and other process residual will be converted to methane in this digester. The methane may be utilized as boiler fuel and reclaimed for process heat requirements. The remaining liquid is sent to an aerobic digester where chemical and biological oxygen demand are effectively reduced, then to a clarifier where water is separated from solids not converted through the digestion process. Depending on the requirements for discharge or re-use, the effluent may be further treated through reverse osmosis membranes, ozonolysis or a combination thereof. The solid material separated from the clarifier may be directed to a sludge centrifuge and de-watering press for concentration to approximately 25% solids content prior to being subjected to alternative disposal. Vents from the process may be subject to de-misting prior to being directed to the atmosphere or boiler as the case may be. Liquid from the de-mister is directed to the anaerobic digester.

Other Fermantation Products

It will be appreciated by those skilled in the art that other fermentation products can result by varying the process described in this Example. For example, use of an alternate fermentation agent such as *Asperigullus niger* under the appropriate conditions can result in the production of citric acid. Use of other fermentation agents or variations in production conditions can result in the production of butanol or isopropanol.

EXAMPLE 2

The biomass materials utilized in this Example are the same as those described above in Example 1. The virgin biomass, non-virgin biomass and cellulase enzymes are prepared as in Example 1.

Preparation of Ethanol

In this Example, simultaneous fermentation of hexose and pentose sugars is employed and no separation of cellulose from pentose is undertaken. After assaying the material using known techniques, about forty equivalent parts pretreated virgin biomass is transferred from the holding tank to a stainless steel jacketed and agitated fermentation vessel. An initial charge of one equivalent part cellulosic material from non-virgin biomass is made prior to adjusting and holding the temperature within the expected range of 30–45° C. and charging enzymes and bacteria. The pH of the mixture is continuously monitored, adjusted and held within the expected range of 6.0–8.0. Cellulase enzymes produced previously are charged at a loading level expected to be between 3.0–10.0 international units per gram of cellulose. In this Example, a *Zymomonas mobilis* of *Escherichia coli* strain is employed for fermentation and is charged at this time as well. The hydrolysis and fermentation process is continuously monitored through common gas or liquid chromatographic techniques and the rate of hydrolysis and fermentation is continuously compared to known rates for virgin biomass. It is expected that after 5–15 hours, the rate comparison will indicate additional loading of non-virgin material is appropriate. One additional equivalent part is charged and appropriate adjustments to enzyme and bacteria feeds may be made. The fermentation process is expected to continue for a total of 100–200 hours with the rates of conversion being continuously monitored and compared to known virgin material conversion rates. It is expected that the ethanol yield and rate will be approximately the same as those of virgin material conversion within acceptable statistical deviations.

Purification of Ethanol and Waste Treatment

When fermentation is complete, the mixture is purified and wastes handled essentially as described above in Example 1.

EXAMPLE 3

In this Example, a mixture of 45% municipal solid waste (MSW), 20% construction and demolition debris, 20% waste paper and 15% soft woods are utilized as non-virgin biomass and are procured from any available source. For example, MSW can be obtained from a compactor truck performing routine pick-up in a rural or urban community or from a transfer station in a like area; construction and demolition debris can be obtained from a commercial roll-off container from a commercial or residential construction site; waste paper can be obtained from commercial or residential recycling programs or enterprises; and softwood can be obtained from logging operations. The virgin biomass in this Example is a mixture of approximately 50% hard wood chips, 25% residue from cranberry harvesting, 15% food processing waste and 10% yard waste.

The virgin biomass, non-virgin biomass, cellulase enzymes, ethanol and purification of ethanol and waste treatment are prepared as described in Example 1.

It is expected that the ethanol yield and rate will be approximately the same as those of virgin material conversion within acceptable statistical deviations.

EXAMPLE 4

In this Example, the biomass materials utilized in Example 3 are used. The virgin biomass, non-virgin biomass and cellulase enzymes are prepared as in Example 1.

Preparation of Ethanol

Simultaneous fermentation of hexose and pentose sugars is employed as in Example 2. It is expected that the ethanol yield and rate will be approximately the same as those of virgin material conversion within acceptable statistical deviations.

Purification of Ethanol and Waste Treatment

When fermentation is complete, the mixture is purified and wastes handled essentially as in described above Example 1.

EXAMPLE 5

In this Example, the biomass materials utilized in Example 1 are used.

Preparation of Virgin Biomass

The virgin biomass is prepared as in Example 1.

Preparation of Non-Virgin Biomass

The non-virgin biomass is subjected to primary processing such that certain items deleterious to the conversion of biomass to ethanol are manually and mechanically separated. Larger materials are first manually removed followed by the trommeling of the material to separate materials by size. Magnetic and eddy current separators and air classifiers are utilized to remove ferrous and non-ferrous metals, glass, plastics, concrete, asphalt and grit, dirt and other non-fermentable materials or materials deleterious to the conversion of biomass to ethanol. When this primary processing is complete, the material is then subject to the further processing steps described above in Example 1.

The separate fermentation of hexose and pentose sugars is employed and the separation is undertaken as in Example 1. The cellulase enzymes are prepared as in Example 1.

Preparation of Ethanol

Fermentation is undertaken as in Example 1 except that only two (2) equivalent parts virgin biomass are expected to be utilized. It is anticipated that the ethanol yield and rate will be approximately the same as those of virgin material conversion within acceptable statistical deviations.

Purification of Ethanol and Waste Treatment

When fermentation is complete, the mixture is purified and wastes handled as described above in Example 1.

EXAMPLE 6

In this Example, the biomass materials utilized in Example 1 are used. The virgin biomass and the cellulase enzymes are prepared as in Example 2.

Preparation of Non-Virgin Biomass

The non-virgin biomass is subjected to primary processing as in Example 5, and then to preparation as described in Example 2.

Preparation of Ethanol

Fermentation is undertaken as in Example 2 except that only two (2) equivalent parts virgin biomass are expected to be utilized. It is anticipated that the ethanol yield and rate will be approximately the same as those of virgin material conversion within acceptable statistical deviations.

Purification of Ethanol and Waste Treatment

When fermentation is complete, the mixture is purified and wastes handled as described above in Example 1.

EXAMPLE 7

In this Example, the biomass materials utilized in Example 3 are used. The virgin biomass and cellulase enzymes are prepared as in Example 3.

Preparation of Non-Virgin Biomass

The non-virgin biomass is subjected to primary processing as in Example 5, and then to preparation as described in Example 3.

Separation of Materials

Separate fermentation of hexose and pentose sugars is employed and the separation is undertaken as in Example 1.

Preparation of Ethanol

Fermentation is undertaken as in Example 3 except that only two (2) equivalent parts virgin biomass are expected to be utilized. It is anticipated that the ethanol yield and rate will be approximately the same as those of virgin material conversion within acceptable statistical deviations.

Purification of Ethanol and Waste Treatment

When fermentation is complete, the mixture is purified and wastes handled as described above in Example 1.

EXAMPLE 8

In this Example, the biomass materials utilized in Example 3 are used. The virgin biomass and cellulase enzymes are prepared as in Example 1.

Preparation of Non-Virgin Biomass

The non-virgin biomass is subjected to primary processing as in Example 5, and then to preparation as described in Example 1.

Preparation of Ethanol

Fermentation is undertaken as in Example 2 except that only two (2) equivalent parts virgin biomass are expected to be utilized. It is anticipated that the ethanol yield and rate will be about the same as those of virgin material conversion within acceptable statistical deviations.

Purification of Ethanol and Waste Treatment

When fermentation is complete, the mixture is purified and wastes handled as described above in Example 1.

EXAMPLE 9

In this Example, the biomass materials utilized in Example 1 are used. The virgin biomass and cellulase enzymes are prepared as in Example 1.

Preparation of Non-Virgin Biomass

The non-virgin biomass is subjected to primary processing as described in Example 5 and then to secondary processing wherein the primary processed material is shredded prior to being processed with a trommel, magnets, and air classifier to remove such additional materials deleterious to its conversion to ethanol as enumerated in Example 5. When this secondary processing is complete, the material is then subject to the additional processing steps identified in Example 1.

Separation of Materials

Separate fermentation of hexose and pentose sugars is employed and the separation is undertaken as in Example 1.

Preparation of Ethanol

Fermentation is undertaken as in Example 1 except that non-virgin and virgin biomass are substituted for each other in process and amounts. It is anticipated that the ethanol yield and rate will be approximately the same as those of virgin material conversion within acceptable statistical deviations.

Purification of Ethanol and Waste Treatment

When fermentation is complete, the mixture is purified and wastes handled as described above in Example 1.

EXAMPLE 10

In this Example, the biomass materials utilized in Example 1 are used. The virgin biomass and cellulase enzymes are prepared as in Example 1.

Preparation of Non-Virgin Biomass

The non-virgin biomass is subjected to primary processing as in Example 9, and then to preparation as described in Example 1.

Preparation of Ethanol

Fermentation is undertaken as in Example 2 except that non-virgin and virgin biomass are substituted for each other in process and amounts. It is expected that the ethanol yield and rate will be approximately the same as those of virgin material conversion within acceptable statistical deviations.

Purification of Ethanol and Waste Treatment

When fermentation is complete, the mixture is purified and wastes handled as described above in Example 1.

EXAMPLE 11

In this Example, the biomass materials utilized in Example 3 are used. The virgin biomass and cellulase enzymes are prepared as in Example 1.

Preparation of Non-Virgin Biomass

The non-virgin biomass is subject to primary processing as in Example 9, and then to preparation as described in Example 1.

Separation of Materials

Separate fermentation of hexose and pentose sugars is employed and the separation is undertaken as in Example 1.

Preparation of Ethanol

Fermentation is undertaken as in Example 1 other than non-virgin and virgin biomass are substituted for each other in process and amounts. It is expected that the ethanol yield and rate will be approximately the same as those of virgin material conversion within acceptable statistical deviations.

Purification of Ethanol and Waste Treatment

When fermentation is complete, the mixture is purified and wastes handled as described above in Example 1.

EXAMPLE 12

In this Example, the biomass materials utilized in Example 3 are used. The virgin biomass and cellulase enzymes are prepared as described in Example 1.

Preparation of Non-Virgin Biomass

The non-virgin biomass is subject to primary processing as in Example 9, and then to preparation as described in Example 1.

Preparation of Ethanol

Fermentation is undertaken as in Example 2 except that non-virgin and virgin biomass are substituted for each other in process and amounts. It is expected that the ethanol yield and rate will be approximately the same as those of virgin material conversion within acceptable statistical deviations.

Purification of Ethanol and Waste Treatment

When fermentation is complete, the mixture is purified and wastes handled as described above in Example 1.

EXAMPLE 13

In this Example, only the non-virgin biomass utilized in Example 1 is used.

Preparation of Non-Virgin Biomass

The non-virgin biomass is subject to processing as described in Example 9, and then to preparation as described in Example 1.

Separation of Materials

Separate fermentation of hexose and pentose sugars is employed and the separation is undertaken as in Example 1.

Preparation of Cellulase Enzymes

The cellulase enzymes are prepared as in Example 1 except that secondary processed non-virgin biomass is utilized for their production.

Preparation of Ethanol

Fermentation is undertaken as in Example 1 except that only secondary processed non-virgin biomass is utilized. It is anticipated that the ethanol yield and rate will be approximately the same as those of virgin material conversion within acceptable statistical deviations.

Purification of Ethanol and Waste Treatment

When fermentation is complete, the mixture is purified and wastes handled as described above in Example 1.

In this Example, only the non-virgin biomass utilized in Example 1 is used.

Preparation of Non-Virgin Biomass

The non-virgin biomass is subject to processing as described in Example 9, then to preparation as described in Example 1.

Preparation of Cellulase Enzymes

The cellulase enzymes are prepared as in Example 13.

Preparation of Ethanol

Fermentation is undertaken as in Example 2 other than only secondary processed non-virgin biomass is utilized. It is anticipated that the ethanol yield and rate will be approximately the same as those of virgin material conversion within acceptable statistical deviations.

Purification of Ethanol and Waste Treatment

When fermentation is complete, the mixture is purified and wastes handled as described above in Example 1.

EXAMPLE 15

In this Example, only the non-virgin biomass utilized in Example 3 is used.

Preparation of Non-Virgin Biomass

The non-virgin biomass is subject to processing as described in Example 9, and then to preparation as described in Example 1.

Separation of Materials

Separate fermentation of hexose and pentose sugars is employed and the separation is undertaken as in Example 1.

Preparation of Cellulase Enzymes

The cellulase enzymes are prepared as in Example 13.

Preparation of Ethanol

Fermentation is undertaken as in Example 1 except that only secondary processed non-virgin biomass is utilized. It is anticipated that the ethanol yield and rate will be approximately the same as those of virgin material conversion within acceptable statistical deviations.

Purification of Ethanol and Waste Treatment

When fermentation is complete, the mixture is purified and wastes handled as described above in Example 1.

EXAMPLE 16

In this Example, only the non-virgin biomass utilized in Example 3 is used.

Preparation of Non-Virgin Biomass

The non-virgin biomass is subject to processing as described in Example 9, and then to preparation as described in Example 1.

Preparation of Cellulase Enzymes

The cellulase enzymes are prepared as in Example 13.

Preparation of Ethanol

Fermentation is undertaken as in Example 2 except that only secondary processed non-virgin biomass is utilized. It is anticipated that the ethanol yield and rate will be approximately the same as those of virgin material conversion within acceptable statistical deviations.

Purification of Ethanol and Waste Treatment

When fermentation is complete, the mixture is purified and wastes handled as described above in Example 1.

It should be appreciated by those skilled in the art that the specific embodiments disclosed above may readily be utilized as a basis for modifying or designing other methods or structures for carrying out the same purpose of the present invention. Such variations are within the scope of the invention. It should also be realized by those skilled in the art that such equivalent constructions do not depart from the spirit and scope of the invention as set forth in the appended claims.

What is claimed is:

1. A method for producing fermentation products from non-virgin biomass, comprising:

providing non-virgin biomass containing convertible biomass and deleterious material, the deleterious material present in an amount sufficient to inhibit conversion of the convertible biomass in the non-virgin biomass to a fermentation product selected from the group consisting of ethanol, citric acid, butanol and isopropanol;

removing at least a portion of the deleterious material present in the non-virgin biomass, thereby producing primary processed non-virgin biomass;

providing virgin biomass, the virgin biomass being substantially without deleterious materials;

combining the primary processed non-virgin biomass with a sufficient amount of the virgin biomass such that remaining deleterious material in the non-virgin biomass is diluted to an extent that conversion to the fermentation product and byproduct of the combination of the primary processed non-virgin biomass and the virgin biomass can be realized;

treating the combination of the primary processed non-virgin biomass and the virgin biomass with hydrolysis and fermentation materials such that conversion to the fermentation product and byproduct occurs from the combination of the primary processed non-virgin biomass and the virgin biomass; and separating the fermentation product from the byproduct.

2. The method as described in claim 1, wherein the virgin biomass is present in an amount between 5–95% by weight and the primary processed non-virgin biomass is present in an amount between 5–95% by weight.

3. The method as described in claim 1, wherein the primary processed non-virgin biomass is subjected to a secondary process prior to the combining the primary processed non-virgin biomass with the virgin biomass, whereby the secondary process removes additional deleterious material from the primary processed non-virgin biomass and produces secondary processed non-virgin biomass, the secondary processed non-virgin biomass then being combined with the virgin biomass.

4. The method described in claim 1, wherein at least a portion of the deleterious material removed from the non-virgin biomass contains recyclable materials.

5. The method as described in claim 1, wherein at least a portion of the deleterious material removed from the non-virgin biomass is suitable for use as landfill material.

* * * * *